United States Patent [19]
Brox

[11] Patent Number: 5,837,675
[45] Date of Patent: Nov. 17, 1998

[54] SYNERGISTIC EFFECT OF INSULIN-LIKE GROWTH FACTOR-I AND ERYTHROPOIETIN

[76] Inventor: Alan G. Brox, 3547 Vendome, Montreal, Quebec, Canada, H4A 3M6

[21] Appl. No.: 383,012

[22] Filed: Feb. 3, 1995

[51] Int. Cl.$^6$ .......................... A61K 38/30; A61K 38/42; A61K 38/00; C07K 14/00
[52] U.S. Cl. ..................................... 514/8; 514/12
[58] Field of Search ............................. 514/8, 12

[56] References Cited

U.S. PATENT DOCUMENTS 5,106,832  4/1992  Froesch et al. ........................... 514/12

OTHER PUBLICATIONS

Zenobi et al., J. Clin. Invest., vol. 89, pp. 1908–1913 (1992).
Clemmors et al., J. Clin. Endocrin. and Metab., vol. 79, No. 1, pp. 4–6 (1994).
Zenobi et al., J. Clin. Invest., vol. 90, pp. 2234–2241 (1992).
Merchav et al., J. Clin. Endocrin. & Metab. vol. 74, No. 2, pp. 447–451 (1992).
Rennick et al., Experimental Hematol., vol. 22, pp. 137–141 (1992).
Lemoli et al., Experimental Hematol., vol. 22, pp. 919–923 (1992).
Sonada et al., J. Am. Society Hematol., vol. 10, pp. 4099–4106 (1994).
Guler et al., N. Engl. J. Orec., vol. 317, pp. 137–140 (1987).
Usala et al., N. Eng. J. Med., vol. 327 No. 12, pp. 853–857 (1992).
Turkalb et al., J. Clin. Endocrin & Metab., vol. 75 pp. 1186–1191 (1992).
Brox et al., 1989, Exp Hematol. 17:769–773.
Congote et al., 1991, J. Clin. Endocrinol. Metab. 72:727–729.
Kurtz et al., 1988, Proc. Natl. Acad. Sci. USA 85:7825–7829.
Boyer et al., 1992, Blood 80:2503–2512.
Sawada et al., 1989, J. Clin. Invest. 83:1701–1709.
Gagnon et al., 1983, Urol. Res. 11:11–14.
Gagnon et al., 1988, Urol. Res. 16:119–126.
Fisher, 1979, J. Lab. Clin. Sci. 93(5):695–699.
Correa et al., 1994, Blood 83:99–102.
Abboud et al., 1991, J. Clin. Invest. 88:470–475.
Philipps et al., 1988, Pediatric. Res. 23:298–305.
Bechensteen et al., 1994, Acta Physiol. Scand, 151:117–123.
Drop et al., 1992, Growth Reg. 2:69–79.
Rechler et al., 1992, Growth Reg. 2:55–68.
Blat et al., 1994, J. Clin. Invest. 93:2286–2290.
Carlsson–Skwirut et al., 1989, Biochem. Biophys. Acta 1011:192–197.
Cascieri et al., 1989, J. Cell. Physiol. 139:181–188.
Bell et al., 1986, Nucl. Acids Res. 14:7873–7882.
Shoemaker et al., 1986, Mol. Cell. Biol. 6:849–858.
Adams et al., 1991, Science 252:1651–1656.
Beru et al., 1986, Mol. Cell. Biol. 6:2571–2575.
Drabkin et al., 1935, J. Biological Chem. 112:51–65.
Eilers, 1967, Am. J. Clin. Pathol. 47:212–214.
Cascieri et al., 1989, J. Biol. Chem. 264:2199–2202.
Francis et al., 1992, J. Mol. Endocrinol. 8:213–223.
Cohick et al., 1993, Annual Rev. Physiol. 55:131–153.
Gordon et al., 1987, Nature 326:403–405.
Roberts et al., 1988, Nature 332:376–378.
Clemmons et al., 1983, J. Clin. Endocrinol. Metab. 56:384–389.
Summers et al., 1988, Texas Agricultural Experimental Station Bulletin No. 1555.
Tsarfaty et al., 1994, Exp. Hematol. 22:1273–1277.

Primary Examiner—Elizabeth C. Weimar
Assistant Examiner—P. Lynn Touzeau

[57] ABSTRACT

Erythropoietin (EPO) and insulin-like growth factor (IGF); pharmaceutical compositions thereof and therapeutic and prophylactic methods to increase the hematocrit are disclosed herein. Increase in hematocrit and reticulocyte count is observed by IGF-I treatment alone or in combination with an other cytokine or growth factor. Also disclosed is the synergistic effect of EPO and IGF-I on hematocrit and reticulocyte count, and the use thereof for treating disease associated with a low erythropoietin level.

11 Claims, 2 Drawing Sheets

SYNERGISTIC EFFECT OF INSULIN-LIKE GROWTH FACTOR-I AND ERYTHROPOIETIN

BACKGROUND OF THE INVENTION

1. Field of the Invention

The present invention in the field of medicine relates to erythropoietin (EPO) and insulin-like growth factors; to pharmaceutical compositions thereof and to therapeutic and prophylactic methods to increase the hematocrit. The invention also relates to IGF binding proteins, and to the increase in hematocrit observed by IGF treatment alone or in combination with another growth factor. More specifically, the invention relates to the synergistic effect of EPO and IGF-I on hematocrit and the use thereof for treating anemia in patients.

2. Description of the Prior Art

In spite of advances in prevention, dialysis, and kidney transplantation, chronic renal failure (CRF) remains a major clinical problem. In addition to the obvious expense associated with dialysis, much of the cost to the individual and society arises from associated conditions including the normochromic normocytic anemia. Although therapy with recombinant erythropoietin (EPO) can improve both the anemia and quality of life, it remains expensive and often requires very large doses. Previous studies on anephric patients presented the first indication in humans that insulin-like growth factor-I (IGF-I) may play an important role in the body's adjustment to depletion of the renal mass and subsequent diminution of the source of EPO (Brox et al., 1989, Exp. Hematol. 17:769–773; and Congote et al., 1991, J. Clin. Endocrinol. Metab. 72:727–729). This work has since been confirmed in several laboratories (Kurtz et al., 1988, Proc. Natl. Acad. Sci. U.S.A. 85:7825–7829; Boyer et al., 1992, Blood 80:2503–2512; and Sawada et al., 1989, J. Clin. Invest. 83:1701–1709). However, an impediment to further progress has been the lack of a suitable animal model in which to dissect the complex metabolic interactions, and to test the effectiveness of therapeutic interventions. This application intends to extend the initial observations on the hormonal response to CRF in a murine model, specifically focusing on the role of IGF-I and its binding proteins.

To develop a more effective rationale to manage the anemia of CRF, one must better understand the interplay of compensatory mechanisms. This can be accomplished by viewing the coordinated actions of EPO and IGF-I through the following two experimental approaches: (1) at the cellular level using bone marrow cultures to identify the relevant targets directly, and (2) in the intact animal using mice with CRF (Gagnon et al., 1983, Urol. Res. 11:11–14; and Gagnon et al., 1988, Urol. Res. 16:119–126) to study the interplay between organ systems and how they can be manipulated to the advantage of the organism.

Stem Cells and the Role of Erythropoietin

Under normal conditions EPO stimulates erythroid precursors to mature and prevents apoptosis. When the renal source of EPO is intact, its concentration in serum increases in response to decreased $O_2$ tension. However, when the nephric mass is compromised below a critical level, sufficient EPO is not produced to maintain normal erythropoiesis, and other compensatory mechanisms must supervene (Fisher, 1979, J. Lab. Clin. Sci. 93:695–699). These include hepatic production of EPO, as well as other less well defined erythrogenic factors such as IGF-I.

Evidence that IGF-I has a Role in Erythropoiesis

Evidence that IGF-I contributes to physiologic control of erythropoiesis includes the following observations: (1) Receptors for IGF-I are found on the earliest of erythroid precursors, (2) growth hormone exerts its influence on the hematopoietic system through the presence of IGF-I (3) it directly increases incorporation of $Fe^{59}$ into erythrons in rats (Kurtz et al., 1988, Proc. Natl. Acad. Sci. U.S.A. 85:7825–7829), (4) its concentration in a murine colony forming unit-erythroid (CFU-e) system is reciprocal to that of EPO and its importance increases as the level of EPO decreases (Boyer et al., 1992, Blood 80:2503–2512), (5) it augments the growth of CFU-e in the absence of accessory cells (Sawada et al., 1989, J. Clin. Invest. 83:1701–1709), (6) in vitro it stimulates red cell generation with clonogenic bone marrow cells, (7) similar results of erythroid enhancement with IGF-I occur with the use of both adult and cord blood, and (8) the erythroid progenitor cell polycythemia vera is hypersensitive to IGF-I but not to EPO (Correa et al., 1994, Blood 83:99).

The notion of an autocrine/paracrine mechanism to fine tune the local control of erythrogenic cytokines (Abboud et al., 1991, J. Clin. Invest. 88:470–475) is supported by the identification of message for both IGF-I and its binding proteins in certain cell lines. Administration of IGF-I in vivo reveals the following: (1) newborn rats increase the erythroid activity of their bone marrow (Philipps et al., 1988, Pediatric. Res. 23:298–305), (2) administration to hypophysectomized animals results in weight gain and accelerated erythropoiesis with a brisk reticulocytosis (Kurtz et al., 1988, Proc. Natl. Acad. Sci. U.S.A. 85:7825–7829), and (3) normal adult mice, but not newborn mice, respond by increasing their reticulocyte counts, however, no increase is seen in the number of CFU-e or hematocrit (Bechensteen et al., 1994, Acta Physiol. Scand, 151:117–123). Of importance, in no experiments to date has there been any evidence of an increase in hematocrit (or hemoglobin) with administration of IGF-I. The hematocrit can be defined as the portion of the blood volume occupied by only red blood cells or erythrocytes; it excludes, in large measure, the volume occupied by plasma. Centrifugation of a sample to eliminate all plasma will determine what is called a packed cell volume or hematocrit. Electronically this is calculated from the red blood cell count and the mean cell volume. The discovery of a treatment that would increase the hematocrit of a patient would provide a substantial advantage over present treatments. Such a treatment would be extremely beneficial to treat patients with CRF, or with anemia associated with chronic diseases, inflammatory diseases, or infectious diseases.

IGF-I, Binding Proteins and Truncated Proteins

In addition to controls on secretion and status of receptors, the activity of IGF-I is regulated by binding proteins in the circulation. To date, six have been identified, and the close preservation of sequence between species attests to their significance (Drop et al., 1992, Growth Reg. 2:69–79).

The one best studied, binding protein 3 (BP3), is dependent on growth hormone, is secreted with IGF-I, and may augment its function by controlling release (Rechler et al., 1992, Growth Reg. 2:55–68). In the blood 20% of the IGF-I is carried as a binary 40 kd complex which is capable of crossing the capillary barrier. The rest is carried as a ternary complex which has a molecular weight of 150 kd and includes an acid labile subunit of 85 kd. This complex represents the storage form of IGF-I and is unable to reach the intravascular space in its native form. Recent evidence suggests that proteolysis by serine proteases may cause disaggregation of these large molecular weight forms making IGF-I more bioavailable (Blat et al., 1994, J. Clin. Invest. 93:2286–2290). The exact role of BP3 as well as the other binding proteins awaits definition. Purified or synthetic proteins have conflicting effects depending on their concentration and the timing of their addition to cell cultures. Thus, both inhibitory and stimulatory effects for BP3 have been described. Recent transfection data suggest that in Balb/c fibroblasts the presence of the BP3 gene inhibits cell growth.

The binding proteins BP1 and BP2 are not dependent on growth hormone, are found primarily in the extravascular space, and appear to act as inhibitors of IGF-I function. BP1 plasma levels are largely insulin dependent and result from rapid gene transcription. This 25 kd protein is remarkable in the presence of 18 cysteines of which 12 are found in the N-terminal sequence. This N-terminal sequence participates in ligand binding. The C-terminal end of the molecule participates in IGF-I binding as mutations in this region abolish this activity. The primary site of metabolism and clearance for BP1 is unknown.

In children with renal failure, lower molecular weight binding proteins like BP1 act as active somatomedin inhibitors. These may result from decreased insulin levels and the growth resistant state seen in renal failure which both increase BP1 concentration in the circulation. This is corroborated by animal studies suggesting that both resistance to growth hormone and decrease in insulin level upregulate BP1 expression and concomitantly downregulate IGF-I message. The observed disaggregation of large molecular weight binding proteins during catabolic states argues that such a process might serve to further modulate the activity of the hormone. This may be a consequence of the release of proteases with formation of inhibitory lower molecular weight forms. Candidate proteases have been isolated from patients with renal failure. Much less is known about BP2 although its concentration in milligram quantities is similar to BP3. The regulation and function of this protein await definition. Under certain conditions BP2 can be inhibitory. Examples include secretion of BP2 by leukemic cells that modify access of IGF-I to both leukemic cells and the hemopoietic microenvironment, and secretion by the intestinal cell that blocks access of both endogenous and exogenous IGF-I to its binding site.

The final mechanism regulating the availability of IGF-I depends on mutation of either the protein itself or of IGF-I. Modification of the binding protein itself can alter the activity of IGF-I. A truncated form of IGF-I which lacks the terminal GLY-PRO-GLU has been isolated from fetal brain and observed to simultaneously show decreased affinity for the binding proteins and enhanced activity (Carlsson-Skwirut et al., 1989, Biochem. Biophys. Acta 1011:192–197). Truncated binding proteins also have been described which exhibit decreased affinity for IGF-I (Drop et al., 1992, Growth Reg. 2:69–79). Such modifications provide a mechanism by which local factors can further regulate the action of this growth factor at its final site of action (Cascieri et al., 1989, J Cell. Physiol. 139:181–188; and references therein).

A better understanding of the interactions between IGF-I and its binding proteins could open important avenues for the treatment of anemia in patients. For example, the design of a recombinant IGF-I that would be unresponsive to one of its inhibitory binding proteins would provide a significant advantage for the treatment of anemic patients. Since IGF-II is similar in both structure and function to IGF-I, the same principles apply to IGF-II (i.e.: for the treatment of anemia, and for the design of recombinant IGF-II).

SUMMERY OF THE INVENTION

The present invention seeks to overcome the deficiencies of the prior art.

The present invention seeks to provide a pharmaceutical composition that permits an increase in the hematocrit. In one embodiment, the present invention provides for the treatment of an anemic patient with a pharmaceutical composition comprising IGF-I. In a preferred embodiment, the present invention provides for the treatment of an anemic patient with a pharmaceutical composition comprising EPO and IGF-I. In yet another embodiment, the invention seeks to provide a pharmaceutical composition which comprises IGF-II.

In accordance with the present invention, there is provided a method of increasing hemoglobin level in an animal, comprising an administration to said animal of an effective, physiologically acceptable amount of insulin-like growth factor. In another embodiment, the insulin-like growth factor administered is in a composition which further comprises at least another growth factor.

In accordance with the present invention, there is also provided a method of preventing apoptosis in an animal, comprising an administration to said animal of an effective, physiologically acceptable amount of insulin-like growth factor. As well, there is provided a hemoglobin level enhancing pharmaceutical composition comprising an effective, physiologically acceptable amount of insulin-like growth factor-I in association with a pharmaceutically acceptable carrier.

In the specification and appended claims, the term pharmaceutical composition should be interpreted as including veterinary compositions. Thus, pharmaceutical compositions of the present invention can be used for the treatment of chronic diseases in animals. The term chronic disease therein, is meant to include but is not limited to chronic infections in general. Examples of chronic infections include but are not limited to tuberculosis, different lung abscesses, subacute bacterial endocarditis. Other examples of chronic diseases comprise various forms of osteomyelitis and inflammatory disease like rheumatoid arthritis, lupus and other collagenoses, various inflammatory diseases of the bowel, including regional enteritis, ulcerative colitis and malignancies in general.

In the specification and appended claims, it should be understood that in addition to IGF-I and IGF-II, other IGF molecules are also contemplated. For example, these include, but are not limited to, homologs of IGF-I and/or IGF-II or recombinant versions (i.e. truncated) of IGF-I and IGF-II or homologs thereof, provided these IGFs retain their biological activity in increasing the level of hemoglobin.

Other features and advantages of the invention will be apparent from the description of the preferred embodiments given hereinafter. However, it should be understood that the detailed description, while indicating preferred embodiments of the invention, are given by way of illustration only, since various changes and modifications within the spirit and scope of the invention will become apparent to those skilled in the art.

DETAILED DESCRIPTION OF THE INVENTION

Effect of Erythropoietin and IGF-I on a Model Erythroid Cell Line

Figure 1:
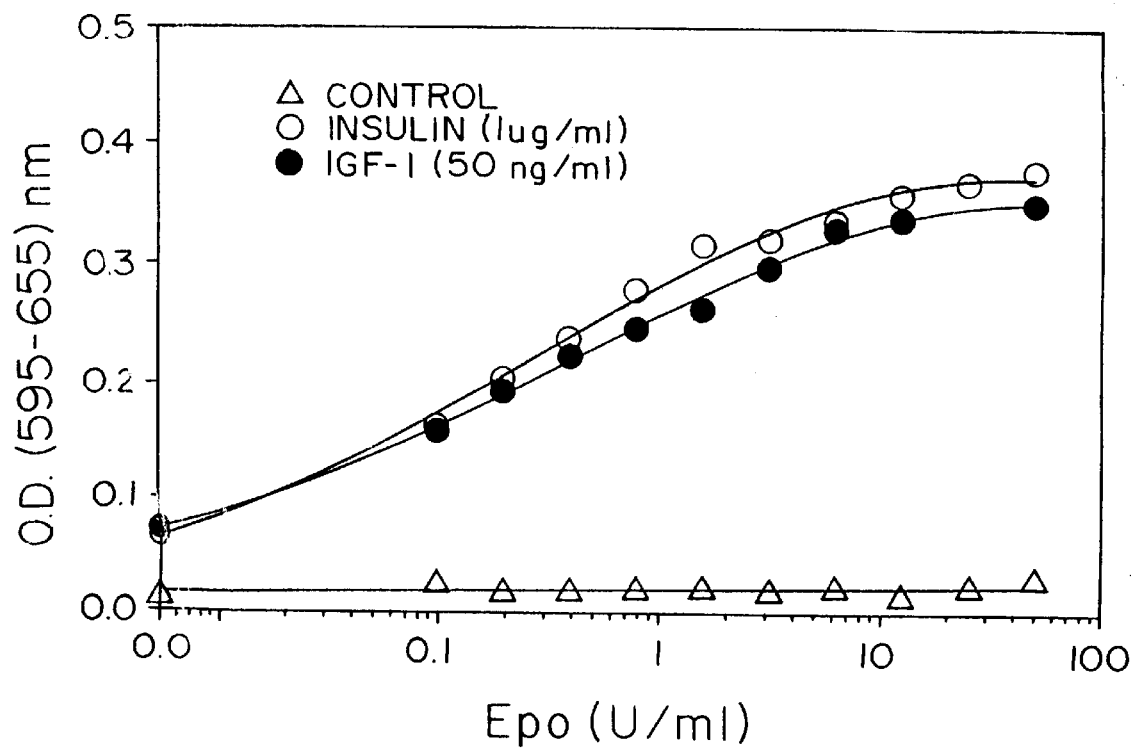
FIG. 1 shows the interaction of erythropoietin with insulin or IGF-I on the proliferation of the MB-02 cell line.
Figure 2:
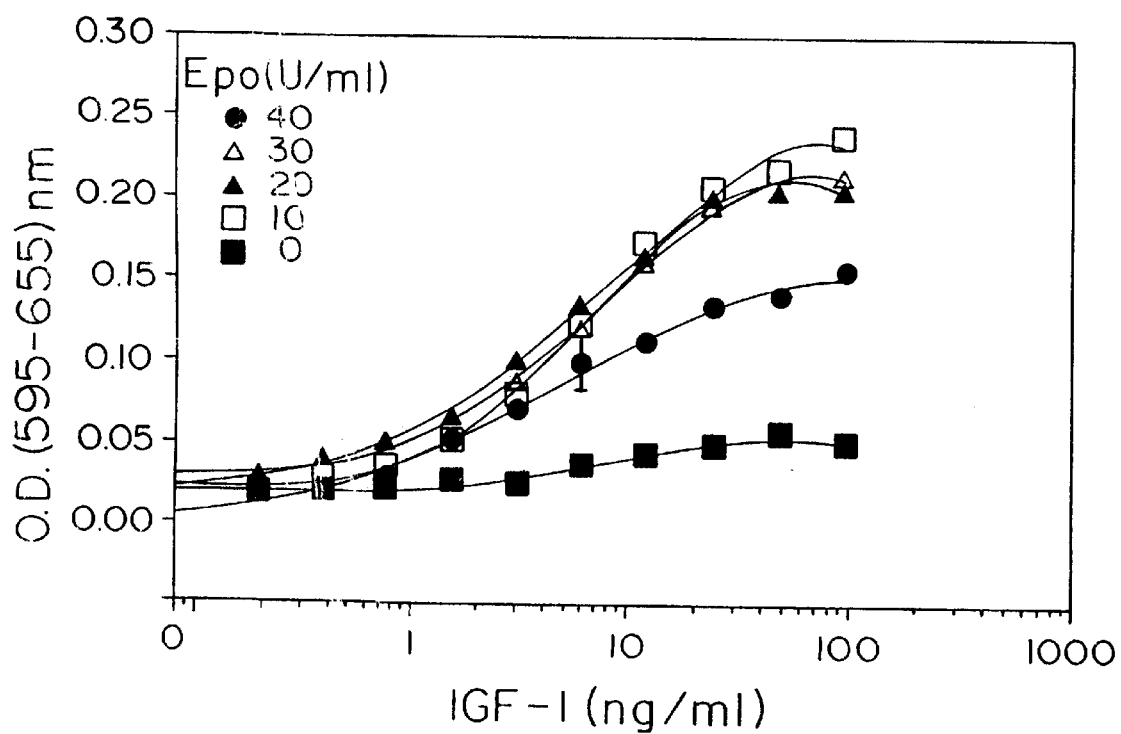
FIG. 2 shows the at least additive effect of IGF-I and EPO, at all concentrations, on the proliferation of the MB-02 cell line.

To dissect and quantify the primary actions of EPO, IGF-I, and IGFBP, it was necessary to develop an in-vitro system. The MB02 cell line with erythroid characteristics (although derived from an individual with acute megakaryocytic leukemia), is shown to proliferate and differentiates in response to EPO, and to a lesser extent, IGF-I (FIG. 1). The effect of the two agents combined was at least additive, demonstrating that at least in an isolated system, both EPO and IGF-I stimulate erythropoietic activity (FIG. 2).

A Murine Model for Chronic Renal Failure

Figure 3:
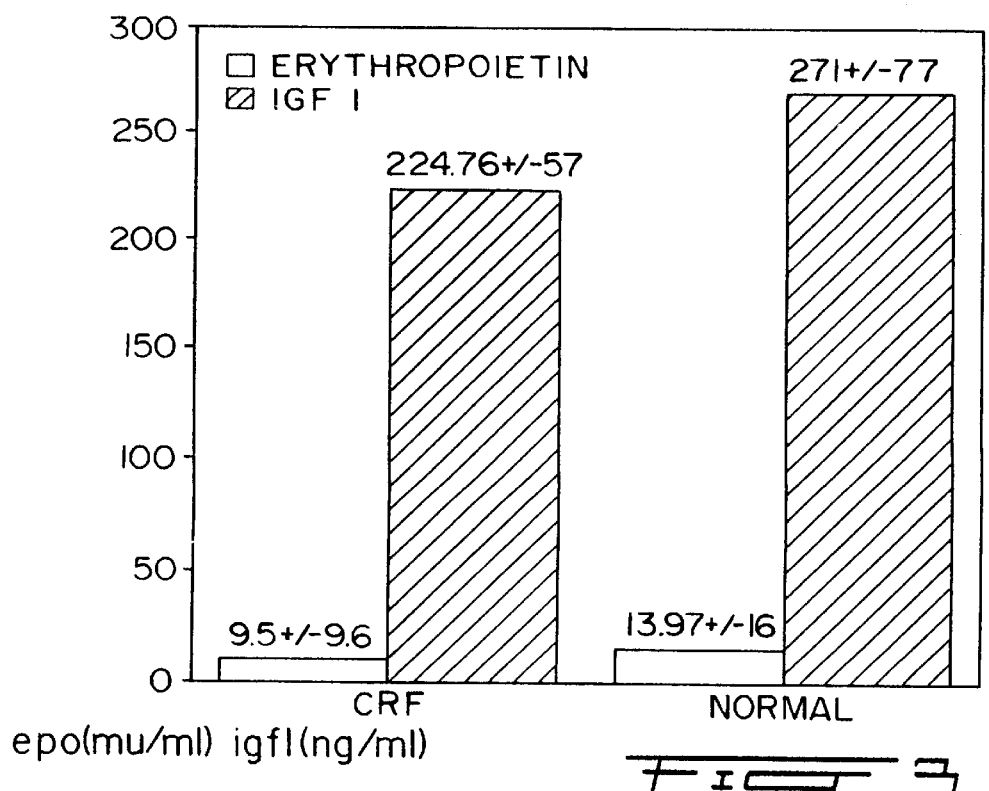
FIG. 3 shows the EPO and IGF-I levels in normal and CRF mice.

To extend these observations on isolated cells, a murine model for CRF that closely mimics the human disease was used (Gagnon et al., 1988, Urol. Res. 16:119–126). Of note, all initial work on EPO was derived from studies using the CRF murine model. As is the case for the human disease, this mouse model shows an elevation of the serum creatinine, hyperparathyroidism, bone loss, artherosclerosis, growth retardation, and a normochromic/normocytic anemia (Gagnon et al., 1988, Urol. Res. 16:119–126). Further, experiments showed that the renal function of the CRF mice was only 20–25% of normal, they were severely anemic, and the concentration of EPO was low. This level of EPO is inappropriately low for the hemoglobin level of these animals (FIG. 3). In the phlebotomized-anemic control animals the EPO level was elevated as expected. Serum EPO levels were measured by radioimmunoassay (Diagnostic Systems Laboratories Inc. and INCSTAR Corporation) according to the manufacturers instructions. Since the animals were neither proteinuric nor showed evidence of hepatic dysfunction, explanations other than EPO deficiency induced by the diminished nephritic mass were sought.

Activation of Genes for Erythropoietic Hormones

To test the hypothesis that the liver might have compensated for the failure of the kidney to produce sufficient EPO to maintain erythropoiesis, mRNA from different organs was surveyed for expression of EPO'and IGF-I message. This approach would circumvent difficulties in interpretation of direct measurements of the hormones because of possible changes in secretion pattern, sequestration, rate of turnover, or degradation. Thus, it was essential to begin to investigate the expression of EPO and IGF-I at the level of gene expression.

Animals used were sacrificed using rapid exposure to carbon dioxide for one to two minutes. Sacrifice of the animals was always performed in the early morning in a non-fasting state. At the time of sacrifice, samples of the kidneys, liver and bone marrow were collected sequentially, snap-frozen and stored in liquid nitrogen for subsequent determination of mRNA expression. The right lobe of the liver was resected following aseptic entry into the peritoneal cavity. The kidneys of normal and renal failure mice were removed following blunt dissection of the retroperitoneal space. Following isolation of both femurs, bone marrow cells were obtained by flushing the bone marrow cavity of both femurs with alpha medium.

For the anemia-induced animal, the anemia was induced acutely in normal mice by controlled phlebotomy under general anesthesia with carbon dioxide. Using a Pasteur pipette, a small volume of blood (0.4 to 0.5 ml) was collected from the retro-orbital venous plexus. This procedure was repeated on three successive days. The phlebotomized mice were studied on the fourth day at the time of sacrifice. In preliminary studies, this approach was shown to induce a reproducible, severe anemia.

Southern blot analysis following RT-PCR was carried out to measure the level of gene expression of EPO and IGF-I. For RT-PCR, total cell RNA was isolated by acid guanididium thiocyanate-phenol- chloroform extraction and any residual contaminating genomic DNA was eliminated by digestion with one unit of DNAse I (Pharmacia, Baie d'Urfé, Quebec, Canada) at 37° C. for 10 minutes. The reaction was stopped by heating samples to 95° C. for five minutes. RNA was reverse transcribed and IGF-I, EPO and β-actin sequences were amplified by the polymerase chain reaction (ie, RT-PCR), using reagents supplied in the Gene Amp Thermostable rTth™ Reverse Transcriptase RNA PCR Kit™ from Perkin Elmer Cetus (Norwalk, LT), following procedures recommended by the manufacturer. The reaction mixtures for reverse transcription were carried out in 0.5 mL microfuge tubes and included 250 ng for β-actin or IGF-I RNA and 50 ng for EPO RNA, 1× reverse transcriptase buffer, 200 uM dNTPs, five units rTth™ polymerase and, 0.15 uM downstream primer in a total volume of 20 uL overlaid with 100 uL of mineral oil. Samples were incubated at 70° C. for five minutes and the reaction was stopped by cooling samples on ice. PCR reaction mixtures were prepared by adding 80 uL of solution containing 1× chelating buffer, $MgCl_2$ (1 mM final concentration), and the upstream primer was added (0.15 uM final concentration) to the reverse transcriptase mixtures in a total volume of 100 uL. Temperature cycling was performed in a Perkin-Elmer Cetus DNA Thermal Cycler using the following protocol; 94° C. for five minutes×one cycle, 60° C. for five minutes×one cycle, (72° C. for 1.5 minutes, 94° C. for 45 seconds, 60° C. for 45 seconds)×35 cycles and 72° C. for 10 minutes×one cycle. The sequences of the primers used were as follows: Mouse EPO upstream, 5'-AGGAGGCAGAAATGTCACGATG-3'; Mouse EPO downstream, 5'-TGTTCGGAGTGGAGCAG-3'; IGF-I upstream 5'-GCACCTCAGACAGGCATTGT-3'; IGF-I downstream, 5'-GGCTCCTCCTACATTCTGTA-3'T; β-actin-upstream, 5'-GTGGGCCGCTCTAGGCACCA-3'; and β-actin-downstream, 5'-CGGTTGGCCTTAGGGTTCAGGGGGG-3'. Oligos for IGF-I and EPO were synthesized using published sequences (Bell et al., 1986, Nucleic Acid Res. 14:7873; and Shoemaker et al., 1986, Mol. Cell. Biol. 6:849) whereas the β-actin primers were obtained from a commercial source (Stratagene, La. Jolla, Calif.). The predicted size of the amplified fragments is 419 bp for EPO, 215 bp (IGF-Ia) and 267 bp (IGF-Ib) for the two alternatively spliced messages of IGF-I, and 245 bp for β-actin.

For Southern blotting analysis, 20 ul aliquots from the PCR samples were resolved by 2% agarose gel electrophoresis. Gels were stained with ethidium bromide and photographed before transfer to nylon membrane (Boehringer Manheim, Laval, Quebec) by the method of Southern using standard procedures. Membranes were pre-hybridized at 42° C. for two hours in 6×SSC, 10×Denhardt's solution, 0.5% sodium dodecyl sulfate (SDS, Terochem Scientific, Canada) and, 50 µg/mL herring sperm DNA (Boehringer Manheim, Laval, Quebec). cDNA probes were labelled with [$^{32}$P]-dCTP (ICN Biomedicals Canada Ltd., Mississauga, Ontario) to a high specific activity (typically $1-2\times10^9$ dpm/µg), by the random primer method using a commercial kit (Multiprime™, Amersham Canada Ltd., Oakville, Ontario). Hybridization was carried out overnight at 42° C. in 50% formamide (Gibco-BRL, Burlington, Ontario), 5×SSC, 10% dextran-sulfate (Pharmacia, Baie D'Urfe Quebec), 0.5% SDS and 50 µg/mL herring sperm DNA. Membranes were subsequently washed twice in 6×SSC, 0.1% SDS for 15 minutes at room temperature; twice in 1×SSC, 0.5% SDS for 15 minutes at 37° C.; once in 0.1% SSC, 0.5% SDS for 30 minutes at 65° C., and exposed to Kodak X-AR5™ film. The probes used were as follows; 0.72 kb EcoRI insert from the plasmid pmigf1-2[50] containing murine IGF-Ia sequences (obtained from the American Type Culture Collection, Rockville, Md.); and the 3.0 kb EcoRI insert from the plasmid HHCI89 (Adams et al., 1991, Science 252:1651) containing human β-actin cDNA sequences (obtained from the American Type Culture Collection, Rockville, Md.). The probe used for EPO was as follows; 1.1 kb, Pst1 insert from the plasmid MSEP1.1 (Beru et al., 1986, Mol. Cell. Biol. 6:2571) containing murine genomic EPO sequences including exons 2, 3 and part of exon 4 (obtained from Dr. Prem Ponka, Jewish General Hospital, Montreal).

Southern blot analysis of the RT-PCR product showed that the EPO message was not detected in the bone marrow of any of the three groups of mice (normal, CRF, and phlebotomized anemic) although message was readily detected (as expected) in the kidneys and livers of phlebotomized animals. Furthermore, the CRF animals did not express EPO in liver or in bone marrow. Conversely, the IGF-I, message was detected in all organs tested from all groups of animals, with the highest concentration found in the liver. The presence of IGF-I message in the bone marrow of all three experimental groups supports the notion that it may be part of an autocrine/paracrine mechanism.

IGF-I and Binding Protein Response

Since EPO message did not increase in CRF and since the liver was not able to supply the difference, the protein levels of IGF-I were assessed in order to verify whether a compensation could occur through an elevation in IGF-I. Such a compensatory mechanism was not observed however, since the levels of IGF-I were similar in all three groups. The protein levels were identified using western blotting analysis. Briefly, 1.0 μl of sera was diluted in 20 μl PBS buffer and 20 μl sodium-dodecyl-sulphate (SDS)-sample buffer without added reducing agent. The sample was heated at 95° C. for five minutes, and then run on 12.5% SDS-polyacrylamide gel electrophoresis mini-apparatus (mini-Gel, Bio-Rad). The molecular weight samples (Bio-Rad Laboratory) were included in the run. Electrophoresis was run at 200 volts for 40 minutes. The separated proteins were transferred by wet-blotting (Trans-blot, Bio-Rad) to nitrocellulose transfer membranes (Millipore) at 30 volts overnight in transfer buffer (0.02 mol/L Trizma base and 0.2 mol/L glycine in 20% methanol-50% distilled water. Membranes were blocked for two hours at 4° C. with 4% milk powder with 0.1% NP-40 (non-ionic detergent) to occupy nonspecific binding sites). Membranes were then incubated overnight with $^{125}$I-IGF-I, washed extensively with PBS buffer, then air-dried and exposed to autoradiographic film for two days, and developed.

The serum IGF-I levels were measured by direct radioimmunoassay (RIA) without extraction following published procedures. The RIA used antiserum UBK487 provided by the National Pituitary Agency (NIAMDD), courtesy of Dr. L. Underwood and Dr. J. J. Van Wyk. This antiserum has a 0.5% cross-reactivity with IGF-II and no crossreactivity with insulin at $10^{-6}$M. Recombinant human IGF-I obtained from Eli Lilly (Indianapolis, USA) was used as a standard. Standard and serum samples at three separate dilutions (1:200, 1:400 and 1:800) were incubated in duplicate with antibody (1:18,000 final dilution) for two hours at room temperature before the addition of radiolabeled IGF-I. After overnight incubation the antibody-bound radiolabeled IGF-I was precipitated using goat and rabbit gamma globulin and normal rabbit serum as a carrier.

Because IGF binding proteins (IGFBP) can modulate the total bioactivity of IGF-I in the circulation, it was critical to investigate whether IGFBP might be responsible for the anemia. The level of IGFBPs was also assessed by Western blotting and showed that in the CRF cohort, both BP1 and BP2 are markedly increased, a pattern consistent in 19 out of 19 animals. Based on these experiments, it is reasonable to propose that a compensatory response to CRF in mice, and possibly other species, is mediated through the action of IGF-I binding proteins.

Figure 4:
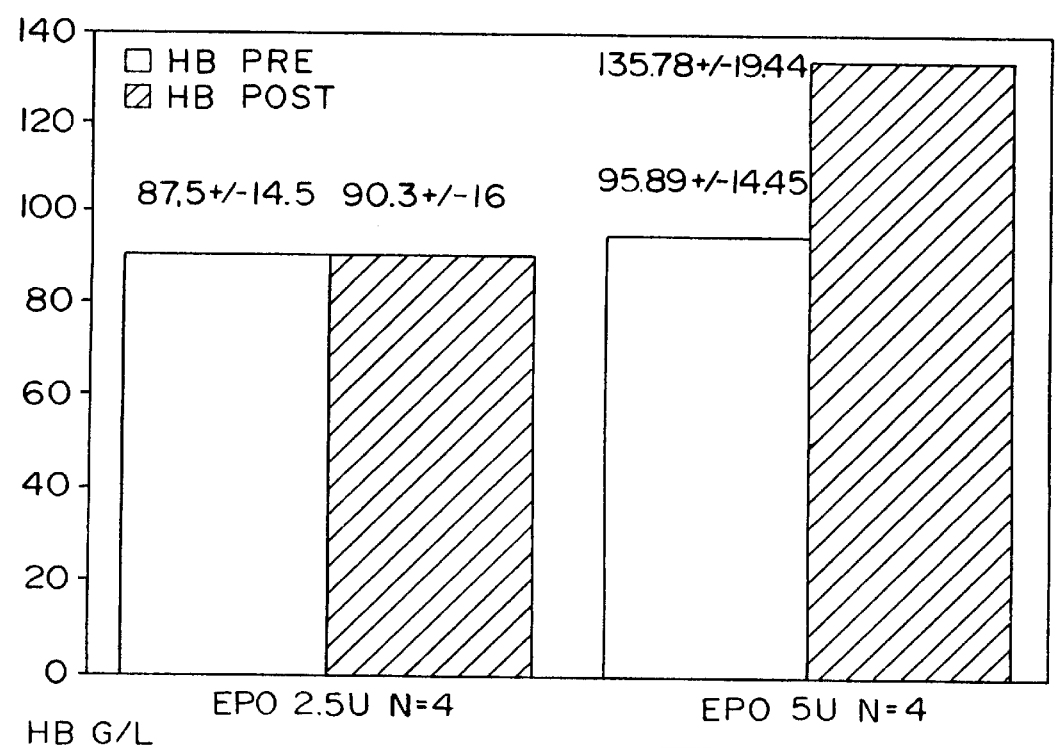
FIG. 4 shows the hemoglobin levels in CRF mice treated with either 2.5 or 5 units of EPO.

Erythropoietin and IGF-I in Combination Synergize to Increase the Hematocrit in Animals with Chronic Renal Failure Similar IGF-I levels in all three groups of animals and the presence of elevated lower molecular weight binding proteins in the renal cohort suggested a state of IGF-I inhibition and or depletion. Experiments designed to replace IGF-I in vivo and to monitor its effect in our renal failure animals were performed. Previous experiments had shown that EPO given subcutaneously as 5 units, three times per week for three weeks stimulated erythropoiesis in our model. Reticulocytes are quantified using thiazole orange and flow cytometry. Importantly, administration of 2.5 units instead of 5 was insufficient to increase the hematocrit (FIG. 4 and Table I). Hemoglobin levels were measured with a quantitative colorimetric assay using cyanmethemoglobin (Drabkin et al., 1935, J. Biological Chem. 112:51, and Eilers, 1967, Am. J. Clin. Pathol. 47:212). When IGF-I at a dose of 2.4 μg was administered subcutaneously to these renal failure animals three of the initial eight animals responded with a significant increase in hemoglobin level (2.2, 2.3 and 4.4 in Table 1). This surprising and significant finding provides an alternative avenue for not only increasing the reticulocyte count, but also the hematocrit.

TABLE 1

Cytokine injection (IGF-I or EPO) in chronic renal failure mice

| | | RETICULOCYTES % | | | HEMOGLOBIN G/L | | |
|---|---|---|---|---|---|---|---|
| Mouse | Rx** | pre Rx | 1 wk post Rx | 3 wks post Rx | pre Rx | 1 wk post Rx | 3 wks post Rx |
| 1.2 | 1 | 2.8 | 8.6 | — | 95 | — | 89 |
| 1.4 | 1 | 3.3 | 8.7 | — | 82 | — | 92 |
| 2.1 | 2 | 2.9 | 6.6 | — | 96 | — | 86 |
| 2.2 | 2 | 2.9 | 8.6 | — | 91 | — | 116 |
| 2.3 | 2 | 4.3 | 8.7 | — | 89 | — | 121 |
| 6A | 2 | 2.3 | 4.9 | — | 67 | — | 82 |
| 4.1 | 3 | 3.6 | 5.7 | — | 77 | — | 83 |
| 4.3 | 3 | 2.7 | 8.1 | — | 88 | — | 94 |
| 4.4 | 3 | 4.4 | 8.8 | — | 87 | — | 112 |
| 6B | 3 | 3.0 | 7.7 | — | 94 | — | 101 |
| 7.1 | none | 5.6 | 6.5 | — | 97 | — | 101 |
| 7.4 | none | 5.1 | 5.9 | — | 81 | — | 86 |
| 1.2 | 4 | 8.6 | 7.2 | 7.5 | 89 | 107 | 107 |
| 1.4 | 4 | 8.7 | 7.4 | 3.0 | 82 | 112 | 101 |
| 4.1 | 5 | 5.7 | 5.7 | 5.5 | 83 | 85 | 75 |
| 4.3 | 5 | 8.1 | QNS | died | 94 | QNS | died |
| 4.4 | 5 | 8.8 | 7.3 | 7.8 | 112 | 113 | 124 |
| 6B | 5 | 7.7 | 6.0 | 7.0 | 101 | 79 | 106 |

**
1 - EPO 2.5 u, sc, 3x/wk × 3 wks
2 - IGF-I 2.4 μg, sc, 3x/wk × 3 wks
3 - IGF-I 2.4 μg, sc, b.i.d.
4 - EPO 5 u, sc, 3x/wk × 3 wks
5 - IGF-I 2.4 μg, sc, 3k/3wk continuously In an attempt to improve on the results with IGF-I alone, both cytokines were combined and showed that the subtherapeutic dose of EPO (2.5 units) when combined with IGF-I (2.4 μg) given subcutaneously, stimulates hemoglobin synthesis in these animals (Table 2). Of great interest is the reproducibility in all animals tested (n=12) and the magnitude of the hemoglobin increase (Table 2).

Thus, a subtherapeutic dose of EPO when combined with IGF-I was as effective as the best EPO dose. The combination of the two cytokines proved superior in efficacy as well as durability of response. Although previous studies have remarked on increases in reticulocytes in vivo following IGF-I use, this is the first demonstration of a significant increase in hematocrit in vivo and suggests that IGF-I in CRF has an important role to play in red cell genesis. It appears therefore, that a feedback loop regulates the response of IGF-I to anemia and/or EPO depletion.

TABLE 2

Chronic renal failure mice treated with a combination therapy of IGF-I and EPO

| | RETICULOCYTES % | | | HEMOGLOBIN G/L | | |
|---|---|---|---|---|---|---|
| Mouse | pre Rx | 1 wk post Rx | 3 wks post Rx | pre Rx | 1 wk post Rx | 3 wks post Rx |
| 5.1 | 4.8 | 8.7 | — | 95 | — | 128 |
| 5.2 | 3.9 | 5.6 | — | 77 | — | 119 |
| 5.3 | 5.8 | QNS | — | 93 | — | 160 |
| 5.4 | 3.3 | 9.7 | — | 87 | — | 127 |
| 2.1* | 6.6 | 8.3 | 9.8 | 86 | 104 | 120 |
| 2.2* | 8.6 | 6.9 | 7.0 | 116 | 126 | 139 |
| 2.3* | 8.7 | 7.5 | 6.7 | 121 | 130 | 172 |
| 6A* | 4.9 | 4.6 | 10.8 | 82 | 80 | 85 |
| 7.1* | 6.5 | 2.4 | 7.0 | 101 | QNS | 135 |
| 7.4* | 5.9 | 6.3 | 5.0 | 86 | 110 | 131 |
| 9.4 | 4.1 | 8.4 | 7.2 | 77 | 92 | 112 |
| 10.3 | 6.6 | 6.2 | 8.3 | 89 | 101 | 147 |
| 10.4 | 6.5 | 7.2 | 6.5 | 76 | 91 | 132 |

*Same mice used for multiple experiments.
All mice in this group received EPO 2.5 u and IGF-I 2.4 μg, sc, 3x/wk × 3 wks.

Based on the response obtained with the CRF murine model, IGF-I alone or in combination with other growth factors, appears ideal for use in treatment of various anemias secondary to other disorders. This can be confirmed using animals with various chronic diseases, inflammatory diseases or infections. These animals can be studied to determine if the initial findings in renal failure can be extended to other anemias associated with low EPO levels. Examples of such anemias associated with a low level of EPO include but are not limited to chronic infections, inflammatory diseases, and malignancies. Examples of inflammatory diseases include rheumatoid arthritis, lupus erythematosus and other collagenoses, but are not limited thereto.

For administration to animals, including humans, in the curative treatment of disease states, the prescribing medical professional will ultimately determine the effective amount to increase hemoglobin level for a given subject, and this can be expected to vary according to the particular pharmaceutical composition (i.e., whether the composition comprises IGF alone or in combination with another cytokine), weight, type of animal and response of the animal as well as the nature and severity of the disease. For example, in a pharmaceutical composition comprising IGF-I, doses of IGF-I ranging from approximately 5 ug/Kg/day to approximately 500 ug/kg/day of animal body weight are contemplated. Preferably, the doses would range from approximately 5 ug/Kg/day to approximately 100 ug/Kg/day of animal body weight. It should be pointed out that the effects of IGF-I on insulin resistance occur in the range of 100 ug/Kg/day to 500 ug/Kg/day. It is also contemplated that periodic treatments or different cycles of treatment with an IGF composition can be beneficial. In one example of a human regimen of IGF-I used in diabetic patients, a dose of 120 ug/Kg/day of patient body weight, is given subcutaneously twice a day for five days. This scheduling for intravenous administration has been described with no real untoward side effects. Weekly doses of 35 mg of IGF given intravenously for insulin resistant hyperglycemia and keto acidosis have also been used in patients for prolonged periods of time, and were not associated with any abnormal side effects. As shown herein, mice received a 2.4 ug dose three times per week for three weeks. In a human patient, this would be equivalent to approximately 8.4 mg three times per week for three weeks.

The route of delivery of IGF alone, or in combination with another cytokine, can also be adapted to meet the required need. For example, routes of administration comprise but are not limited to intravenous, subcutaneous and topical administration. IGF, alone or in combination with another cytokine, a pharmaceutical composition comprising IGF, can also be incorporated in a vesicle such as a liposome but not limited thereto. Infusions comprising IGF can be given as a rapid bolus intravenous infusion, as a continuous infusion over eight hours, or as subcutaneous doses either once or twice a day. Clearly therefore, there is variability in how the medication should be given.

The results with IGF-I on reticulocyte count and hematocrit are apparently due to the inhibition of apoptosis by IGF-I. It also appears that IGF-I stimulates cell division. In view of this, IGF-I can also be used to prevent programmed cell death.

Of importance, since IGF-I is already in use for the treatment of patients with diabetes who are insulin resistant, the results presented herein have short-term implication on the treatment of patients in need of IGF-I. Since the structure-function relationship of IGF-I and IGF-II is so similar, the same is expected for IGF-II as well as other IGFs.

Clues to the mechanism of action of IGFs

The identification of the important role played by IGF-I in erythropoiesis provides numerous avenues aimed at increasing its promoting effect on reticulocyte count and on hematocrit. For example, site-directed mutagenesis of IGFs can lead to an up-regulation of its activity. Because IGF-I is not glycosylated, it can be synthesized in non-mammalian expression systems, and several publications document that modified IGF-I protein can be produced (Cascieri et al., 1989, J. Biol. Chem. 264:2199–2202; Francis et al., 1992, J. Mol. Endocrinol. 8:213–223; and Cohick et al., 1993, Annual Rev. Physiol. 55:131–153 and references therein). A more active IGF-I could for example be produced through modifications affecting its interaction with its receptor, with its binding proteins or with Heparin. IGFBPs contribute to both the stability of IGFs in plasma and their relatively high concentration tolerated in plasma in comparison to other growth factors. These carrier proteins not only compete with the cellular receptors, but also may modify the mechanism of action of the growth factor itself. Thus, changes induced by site directed mutagenesis can eliminate IGFBP binding sites and can diminish the amount of IGFs necessary to stimulate erythropoiesis. Since both IGF-I and IGF-II bind to heparin, more avid binding to glycosaminoglycans might increase IGF activity by two mechanisms. First, the extracellular matrix (ECM) could act as a "physiologic buffer", as it does for other Heparin-binding growth factors (Gordon et al., 1987, Nature 326:403–405) or in the selective compartmentalization of certain hematopoietic growth factors (e.g., GM-CSF or IL-3) (Gordon et al., 1987, Nature 326:403–405; and Roberts et al., 1988, Nature 332:376–378). Secondly, increased Heparin binding could decrease the binding of IGFBPs (Clemmons et al., 1983, J. Clin. Endocrinol. Metab. 56:384–389). Large quantities of recombinant IGF-I (or other recombinant genes encoding proteins interacting therewith) could be obtained using the Baculovirus expression system, which is ideal for the production of large amounts of growth factors required for in vivo experiments (Summers et al., 1988, Texas Agricultural Experimental Station Bulletin No. 1555).

The derivation of a bone marrow precursor cell line system, to dissect the interaction between IGF-I and other growth factors such as EPO on erythropoiesis can provide significant results. Thereby, the role played by the interaction between IGFBPs and IGF-I on the modulation of IGF-I activity on stimulating erythropoietic colonies or on the synergy with EPO can be assessed. For example, neutralization of this activity using commercially available antibodies to the binding proteins can be carried out.

To dissect the effect of IGF-I directly on its cellular targets from its interaction with binding proteins, a series of IGF-I mutants that remain active, but retain only a low affinity of binding to the binding proteins can be prepared. These IGF-I mutants can be tested to determine how they influence erythropoiesis both in vitro and in vivo, in normal and CRF mice, by a strategy similar to that described above for native IGF-I.

Similarly, a hyperactive IGF-I can potentially be a more potent therapeutic agent. One example of a potential hyperactive IGF-I is an EPO-IGF chimera as generated for IL-3/GM-CSF. Such chimera has the potential to be more effective in increasing hemoglobin and reticulocyte count in an animal.

IGF-II or variants thereof or homologs of IGF-I and/or IGF-II or variants thereof can also be useful as erythroid stimulating factors in anemia. IGF-II is similar to IGF-I in both structure and function. Both IGF-I and IGF-II act through the same receptor (Type I) for their mitogenic effects, however IGF-II concentrations in adults are low when compared with IGF-I levels and are independent of growth hormone secretion. IGF-I suppresses growth hormone secretion so that addition of exogenous IGF-I might switch off the endogenous IGF-I production of some patients. Although IGF-II has a higher affinity for the insulin receptor than IGF-I, the hypoglycemic effects of IGF-I are greater than those of IGF-II. Thus, IGF-II alone or in combination with another growth factor such as IGF-I can also potentially be efficacious for increasing hemoglobin in an animal.

In summary using a murine model of chronic renal failure, which mimics the disease seen in humans, it has been shown that IGF-I alone or in combination with EPO is found to have a significant in vivo activity on reticulocyte count and on hematocrit. An increase in hematocrit using IGF-I in vivo had previously never been observed. The response to the combination is as good or better than that achieved with maximal dose of erythropoietin. This is the first in vivo evidence that IGF-I has a physiological role to play in erythropoiesis. Other EPO-deficient states such as that seen with anemia of chronic diseases is envisioned to respond in a similar fashion.

The demonstration that EPO gene expression is absent in liver and bone marrow in the CRF mouse model, questions the role and importance of extrarenal EPO production in this EPO-deficient state. This lends support to the role of IGF-I, IGF-II and other cytokines or growth factors as potential erythropoietic regulators during states of erythropoietin deficiency. Based on the results presented above, the cost of treatment of anemias associated with low EPO levels can be substantially decreased by the use of IGF-I alone, in combination with EPO and/or other growth factors, or a fusion protein between IGF-I and EPO or IGF-I and another cytokine or growth factor. In addition, it appears that other IGFs can be similarly used.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

I claim:

1. Method of increasing nemoglobin level in an anemic mammal having a low level of erythropoietin, comprising an administration to said mammal an effective, physiologically acceptable amount of insulin-like growth factor.

2. The method of claim 1, wherein the insulin-like growth factor is insulin-like growth factor-I.

3. The method of claim 1, wherein the insulin-like growth factor is insulin-like growth factor-II.

4. The method of claim 2, wherein the insulin-like growth factor is in a composition which further comprises at least another growth factor having erythroid promoting activity and a physiologically acceptable carrier.

5. The method of claim 3, wherein the insulin-like growth factor is in a composition which further comprises at least another growth factor having erythroid promoting activity and a physiologically acceptable carrier.

6. The method of claim 4, wherein the at least another growth factor comprises erythropoietin.

7. The method of claim 6, wherein the composition further comprises insulin-like growth factor-II and physiologically acceptable carrier.

8. The method of claim 2, wherein the mammal is a human anemic patient and wherein the anemia is associated with a disease selected from a chronic disease, an inflammatory disease or a chronic infection, wherein said anemia is characterized by being associated with a low level of erythropoietin.

9. The method of claim 4, wherein the mammal is a human anemic patient and wherein the anemia is associated with a disease selected from a chronic disease, an inflammatory disease or a chronic infection, wherein said anemia is characterized by being associated with a low level of erythropoietin.

10. The method of claim 6, wherein the mammal is a human anemic patient and wherein the anemia is associated with a disease selected from a chronic disease, an inflammatory disease or a chronic infection, wherein said anemia is characterized by being associated with a low level of erythropoietin.

11. The method of claim 8, wherein the disease is chronic renal failure, rheumatoid arthritis, or lupus erythematosus.

* * * * *